(12) United States Patent
Eichhorst

(10) Patent No.: US 7,449,009 B2
(45) Date of Patent: Nov. 11, 2008

(54) DEVICE FOR NEEDLE-FREE INJECTION OF A MEDIUM INTO THE TISSUE OF A HUMAN OR AN ANIMAL, DEVICE FOR NEEDLE FREE PRODUCTION OF AN INJECTION CHANNEL AND METHOD FOR THE NEEDLE FREE INJECTION OF A MEDIUM IN THE TISSUE

(75) Inventor: Peter Eichhorst, Hohen Neuendorf (DE)

(73) Assignee: primoJEX GmbH, Hohen Neuendorf (DE)

( * ) Notice: Subject to any disclaimer, the term of this patent is extended or adjusted under 35 U.S.C. 154(b) by 562 days.

(21) Appl. No.: 10/517,928

(22) PCT Filed: Jun. 13, 2003

(86) PCT No.: PCT/DE03/01997

§ 371 (c)(1),
(2), (4) Date: Dec. 14, 2004

(87) PCT Pub. No.: WO03/105934

PCT Pub. Date: Dec. 24, 2003

(65) Prior Publication Data

US 2005/0245859 A1    Nov. 3, 2005

(30) Foreign Application Priority Data

Jun. 14, 2002    (DE)    ................. 102 26 537

(51) Int. Cl.
*A61M 5/30*    (2006.01)
*A61M 5/00*    (2006.01)
*A61M 5/32*    (2006.01)
*A61M 5/315*   (2006.01)

(52) U.S. Cl. ............. 604/68; 604/70; 604/181; 604/187; 604/193; 604/197; 604/218

(58) Field of Classification Search ............. 604/181, 604/183–184, 187, 192, 193–194, 196–197, 604/207, 209, 210, 214, 218, 221, 230, 233, 604/68, 70; 600/433, 435
See application file for complete search history.

(56) References Cited

U.S. PATENT DOCUMENTS 3,057,349 A * 10/1962 Ismach ................. 604/71
3,461,867 A * 8/1969 Hubbard et al. ........... 604/71

(Continued)

FOREIGN PATENT DOCUMENTS

EP    0 286 798    10/1988

(Continued)

*Primary Examiner*—Nicholas D. Lucchesi
*Assistant Examiner*—Quynh-Nhu H Vu
(74) *Attorney, Agent, or Firm*—Collard & Roe, P.C.

(57) ABSTRACT

An injection channel is produced in human or animal tissue by means of a pre-injection device for incorporating a medium which is to be injected. Said pre-injection device comprises a chamber which is used to receive a pre-injection medium, a nozzle which is provided for attachment to the skin and a pressure generating device which acts on the chamber in order to generate a high-pressure jet from the pre-injection medium exiting from the nozzle. Said type of needle-free pre-injection device is serially connected to a main injection device.

21 Claims, 10 Drawing Sheets

U.S. PATENT DOCUMENTS

Figure 1:
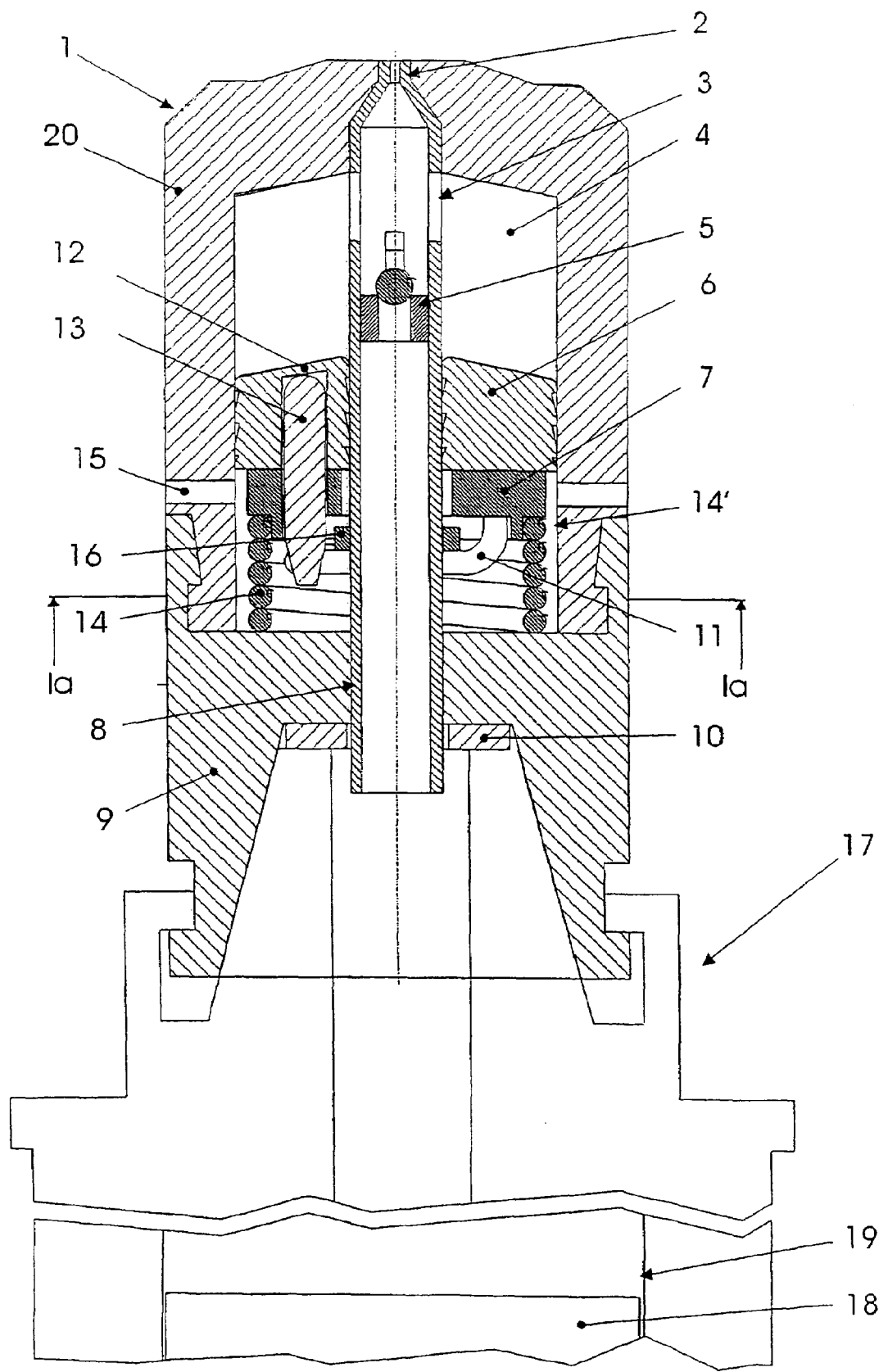

| | | | | |
|---|---|---|---|---|
| 3,805,783 | A | * | 4/1974 | Ismach ..................... 604/71 |
| 4,596,556 | A | * | 6/1986 | Morrow et al. ............... 604/70 |
| 4,722,728 | A | * | 2/1988 | Dixon ...................... 604/68 |
| 5,279,586 | A | | 1/1994 | Balkwill |
| 5,505,343 | A | * | 4/1996 | Knickerbocker ......... 222/321.1 |
| 6,673,035 | B1 | * | 1/2004 | Rice et al. .................. 604/72 |
| 6,689,092 | B2 | * | 2/2004 | Zierenberg et al. ........... 604/68 |

FOREIGN PATENT DOCUMENTS

| | | | |
|---|---|---|---|
| WO | WO98/15307 | | 4/1998 |
| WO | WO01/36028 | | 5/2001 |
| WO | WO01/64268 | | 9/2001 |
| WO | WO01/89613 | | 11/2001 |
| WO | WO 02/49697 | * | 12/2001 |
| WO | WO02/49697 | | 6/2002 |

* cited by examiner

DEVICE FOR NEEDLE-FREE INJECTION OF A MEDIUM INTO THE TISSUE OF A HUMAN OR AN ANIMAL, DEVICE FOR NEEDLE FREE PRODUCTION OF AN INJECTION CHANNEL AND METHOD FOR THE NEEDLE FREE INJECTION OF A MEDIUM IN THE TISSUE

Applicant claims priority under 35 U.S.C 119 of German Application No. 102 26 537.2 filed Jun. 14, 2002. Applicant also claims priority under 35 U.S.C. 365 of PCT/DE03/01997 filed Jun. 13, 2003. The international application under PCT article 21(2) was not published in English.

Device for needle-free injection of a medium into the tissue of a human or an animal, device for needle-free production of an injection channel, and method for needle-free injection of a medium into the tissue The invention relates to a device for needle-free injection of a medium into the tissue of a human or an animal. Furthermore, the invention relates to a device for needle-free production of an injection channel, for introduction of a medium to be injected into the tissue. Furthermore, the invention relates to a method for needle-free injection of a medium into the tissue of a human or an animal.

Needle-free injection devices have become known from WO 98/15307 and WO 01/36028, in which the medium to be injected is introduced into the tissue as a high-pressure jet. In this connection, the medium to be injected produces its injection channel in the tissue on its own. The needle-free injection device has the advantage that no needle is required for the injection. A disadvantage of the needle-free injection device, however, is that the amount of the medium to be injected is limited to approximately 0.4 to 0.5 ml, because of the ability of the tissue to absorb such an amount, injected by means of a high-pressure jet within a short period of time. Therefore, in the case of needle-free injection of media at a higher dose, the risk of not bringing the entire dose to the destination site increases. Larger amounts to be injected by means of a high-pressure jet require higher pressure forces to be applied, thereby resulting in the increased risk of local tissue damage and therefore a greater sensation of pain. Furthermore, in the case of some media, the molecular structure of the medium can be damaged, as a result of the pressure pulses that occur in the needle-free injection device.

Likewise, a structural unit formed of a supply chamber and a needle-free injection device is known from WO 01/64268. The supply chamber and the pump chamber of the needle-free injection device are connected with one another by way of a hollow piston. The hollow piston has a valve at its end, which projects into the pump chamber. If the hollow piston is moved into the pump chamber by means of a pressure production device that is impacted by a spring force, the valve closes, and the amount of the medium to be injected that is located in the pump chamber is injected into the tissue. During this injection, the injection channel is produced in the tissue. With this, the amount of the medium to be injected is strictly limited to 0.4 to 0.5 ml, here as well, since the injection of a larger amount to be injected by means of a high-pressure jet can result in tissue damage. After the injection device was triggered, it can be biased again, in that the hollow piston is moved out of the pressure production device, counter to the spring force. When this is done, medium to be injected gets from the supply chamber into the pump chamber. Subsequently, the next injection can be started. Therefore this injection device has to be biased very frequently for the injection of several ml, and has to be placed on the skin again. However, this also results in a greater sensation of pain and in skin irritation.

Generally known hypodermics for injection, for example of medications or anesthetics in greater volumes than 0.5 ml, for example, into tissue, have a hollow needle that is introduced into the tissue through the skin. With this, the hollow needle produces an injection channel in the tissue. Subsequently, the medium to be injected is pressed into the tissue through the hollow needle. These syringes have the advantage that large amounts of the medium to be injected over a predetermined period of time are gently introduced into the tissue at a low volume flow, and that media with a pressure-sensitive molecular structure can be used. The introduction of large amounts, of several ml, for example, can be carried out with the known syringes, using light manual pressure onto the syringe piston. A disadvantage of such syringes, however, is that the penetration of the skin with a needle is described as painful or disturbing by many patients. In addition, the use of the needle results in a greater risk of infection for the injected organism and for the user.

The invention is based on the problem of further developing a device of the type stated initially, in such a manner that it can be used to inject a greater amount, several ml, for example, into the tissue in needle-free manner. Furthermore, a device is supposed to be created with which an injection channel can be produced in the tissue, in needle-less manner, for subsequent injection of a medium to be injected. Furthermore, a method is supposed to be created, with which several ml of a medium to be injected can be injected into the tissue without a needle and without repeated placement against the skin.

The problem first mentioned is solved, according to the invention, by means of a needle-free pre-injection device for production of a high-pressure jet of a pre-injection medium for producing an injection channel by means of a high pressure and a small volume, and by means of a main injection device for introduction of the medium to be injected, with a great volume and a low pressure in comparison with the volume and pressure of the pre-injection device.

By means of this configuration, an injection channel is first produced using the pre-injection device. The production of the injection channel is produced, as in the case of the known injection devices, by means of a high-pressure jet. In contrast to the known injection devices, however, the amount to be introduced into the tissue for the production of the high-pressure jet can be kept particularly low. With this, it is not necessary, thanks to the invention, to bring the entire amount of the medium to be injected into the tissue as a high-pressure jet, but rather only a very slight amount that is required for the production of the high-pressure jet. As a result, the tissue is handled gently, and this has the result that a large amount of the medium to be injected can be introduced into the tissue by means of the injection channel produced by the high-pressure jet, and distributed in the tissue.

Furthermore, either a physiologically non-problematic liquid, or anesthetics not sensitive to pressure, for anesthetizing the tissue, can be used, for example, as the pre-injection medium, and a medication having a pressure-sensitive molecular structure can be used as the medium to be injected. For this purpose, the device according to the invention has a separate chamber for the pre-injection device and for the main injection device, in each instance. Medications having a pressure-sensitive molecular structure could not be injected in needle-free manner until now, because they are destroyed during the production of the high-pressure jet.

If the medium to be injected has a pressure-stable molecular structure, it can, of course, also be used as the pre-injection medium, at the same time. This has the advantage that only one medium has to be injected. For such an injection, the pre-injection device and the main injection device can have a common chamber, which has pressure applied to it from two pressure production devices having different strength values. As an alternative to this, a single pressure production device can also be used, in which the pressure build-up at first takes place without damping, with a small amount, to produce the high-pressure jet, and subsequently is limited to a low pressure during introduction of the main amount of the medium to be injected, by means of a damper, over a predetermined period of time.

Preferably, the pre-injection device and the main injection device have a common nozzle, whereby a channel that is guided from the chamber of the main injection device to the nozzle contains a kick-back valve. In this connection, the configuration of the nozzle can be round, as in the case of the needle, or non-round, or it can have several individual openings for distribution of the medium to be injected, in the tissue.

The device according to the invention is configured in particularly simple manner and can furthermore be easily handled if a trigger of the pre-injection device is in an activation connection with the main injection device. Here, a pressure is built up in the main injection device, which activates the trigger of the pre-injection device. After the pre-injection device has been triggered, the pressure in the main injection device is sufficient to maintain the injection channel and to introduce the medium to be injected into the tissue.

The second problem mentioned, namely the creation of a device for producing an injection channel in the tissue of a human or an animal, for subsequent injection of a medium to be injected, is solved, according to the invention, in that a pre-injection device is provided ahead of a main injection device that contains the medium to be injected, that a chamber of the pre-injection device provided for accommodation of a pre-injection medium has a nozzle intended to be set onto the skin, and the pre-injection device has a pressure-production device for producing a high-pressure jet of the pre-injection medium that exits from the nozzle, and that the chamber has a volume sized exclusively for producing the injection channel.

In this way, a pre-injection device is created that can be combined with an existing main injection device. The main injection device, for example, can be a conventional syringe, on which the pre-injection device is mounted in place of a needle. Also, the pre-injection device can be mounted on a commercially available so-called PEN injector, in place of a needle. Such PEN injectors are commonly used to inject insulin. Preferably, the pre-injection device has a coupling device with which it can be coupled to the conventional syringes or injectors, in place of a needle.

The third problem mentioned, namely the creation of a method with which several ml of a medium to be injected can be injected into the tissue without a needle and without multiple placement against the skin, is solved, according to the invention, in that first, a high-pressure jet of a pre-injection medium is produced, and an injection channel is produced in the tissue by means of the high-pressure jet, and subsequently, the medium to be injected is introduced into the tissue through the injection channel.

According to the preferred method, an injection channel is first produced through the skin, up to the destination site in the tissue, by means of a high-pressure jet of a pre-injection medium. Subsequently, the medium to be injected can be introduced into the tissue through the injection channel produced by the pre-injection medium. Preferably, when the medium to be injected is introduced, a minimum pressure is produced to maintain the injection channel necessary for the injection. This minimum pressure is produced by means of pressure on the injection medium. Thanks to the invention, it is not necessary to introduce the entire medium to be injected into the tissue as a high-pressure jet, and instead, only the amount that is required in order to produce the injection channel that is made to the planned destination site is introduced as a high-pressure jet. The greater part of the medium can be introduced into the tissue at a significantly lower pressure. With this, a large amount of several ml, for example, can be injected into the tissue. The tissue is handled gently because of the low pressure during introduction of the medium to be injected. In addition, any impairment of the molecular structure of the medium to be injected is avoided. With this, those medications that are destroyed during the pressure buildup for producing the high-pressure jet can be introduced into the tissue in needle-free manner. In comparison with the known methods for needle-free injection, significantly more medications can be injected using the method according to the invention.

There are numerous embodiments of this invention. Several possible exemplary embodiments will be explained using the following description of the drawings.

Figure 1A:
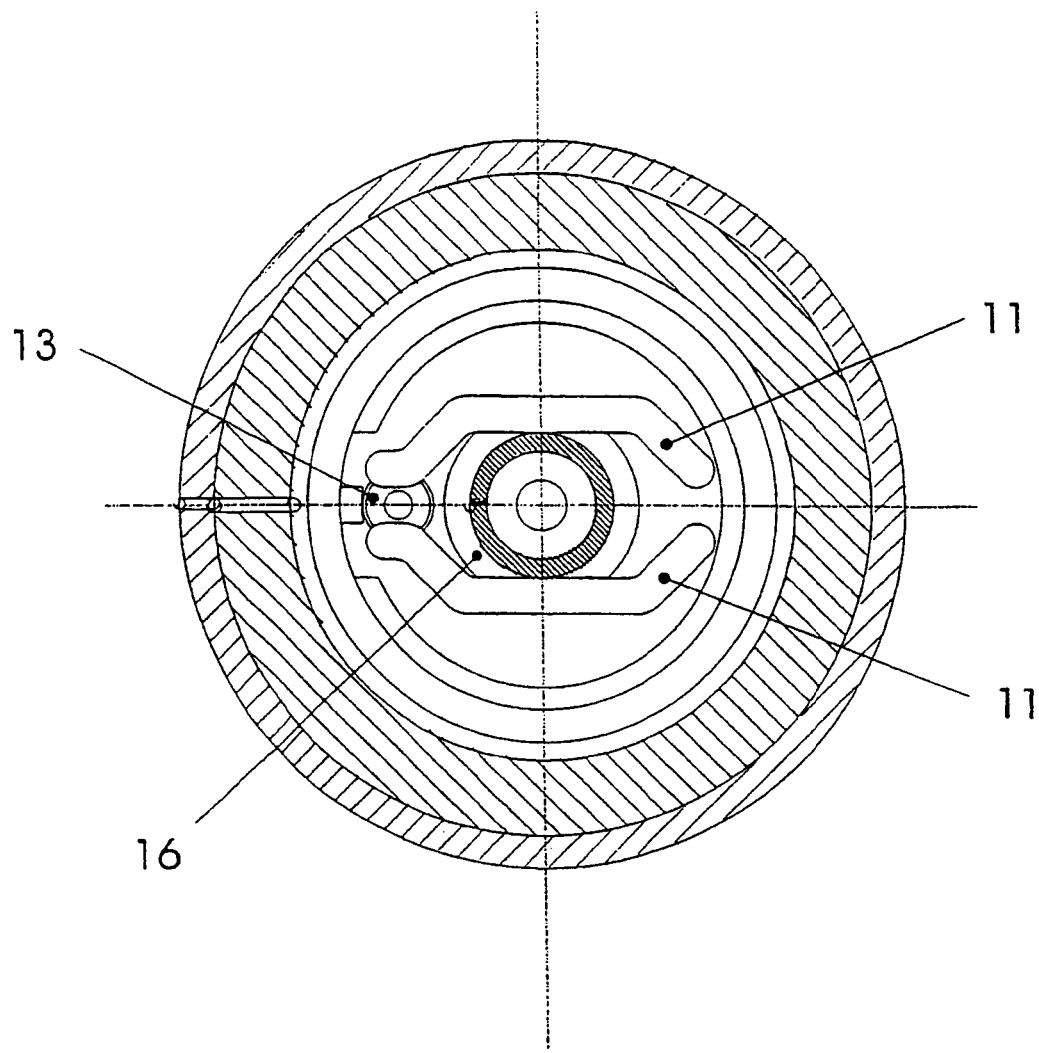
Figure 2:
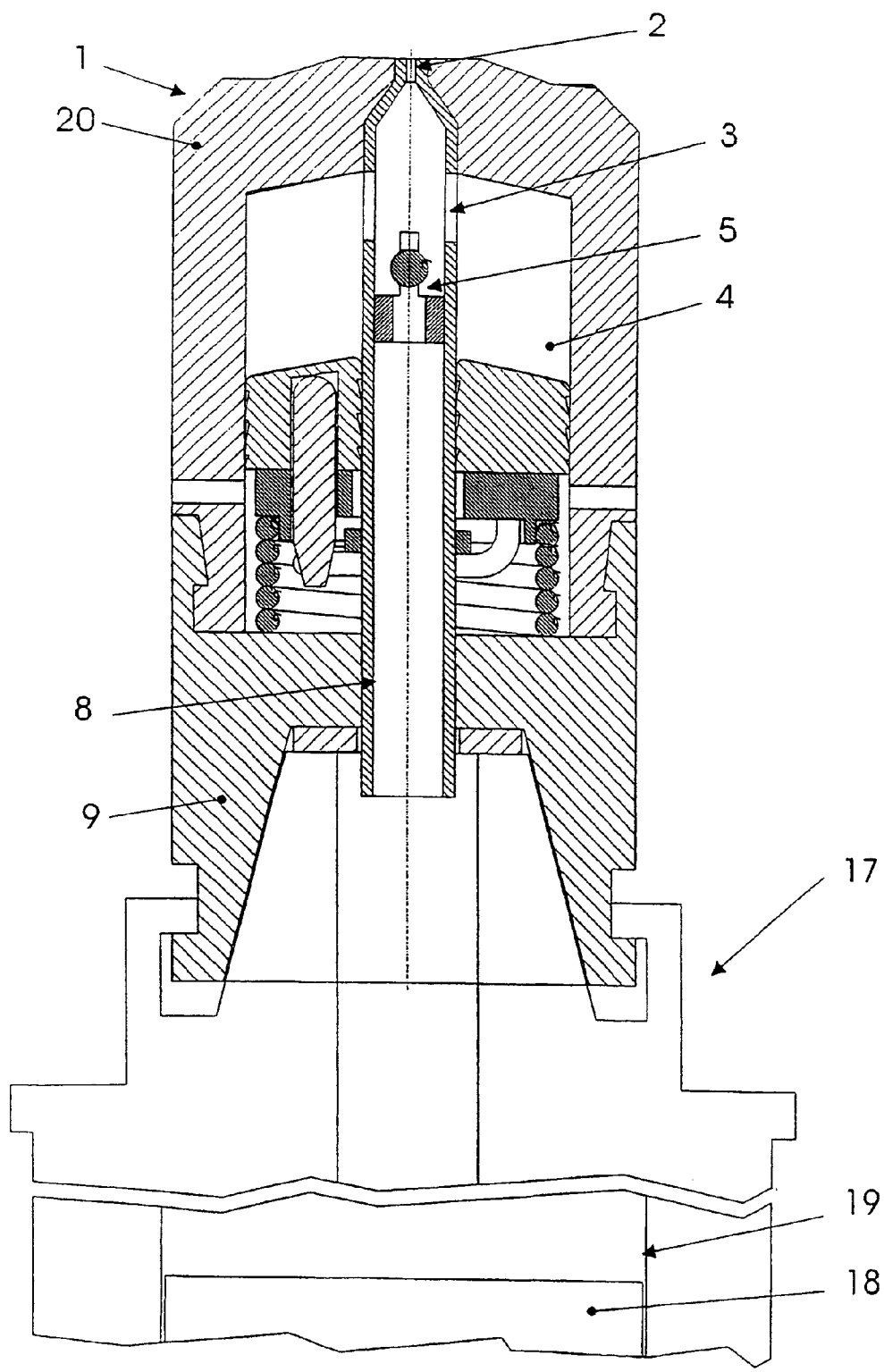
Figure 3:
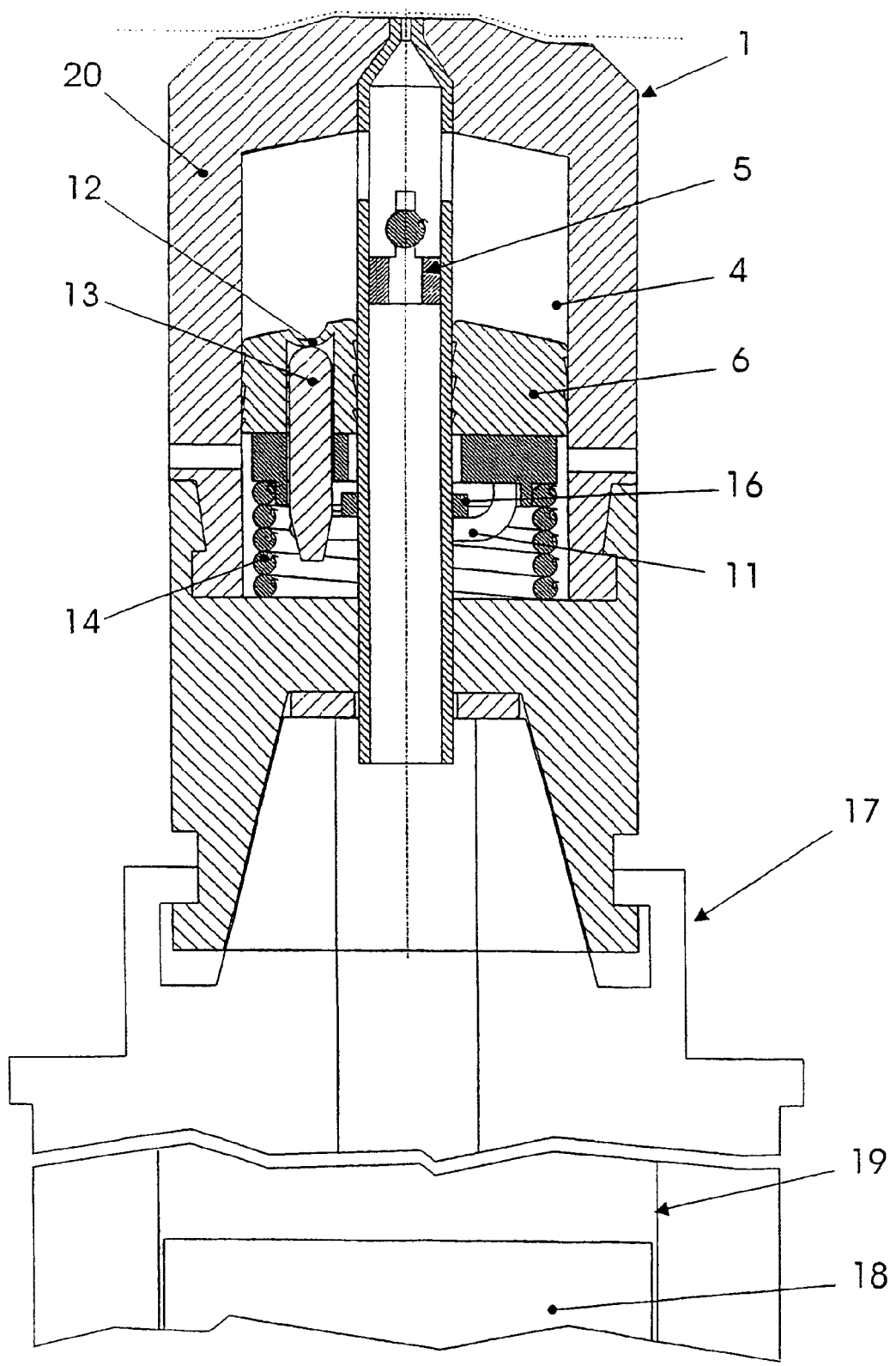
Figure 4:
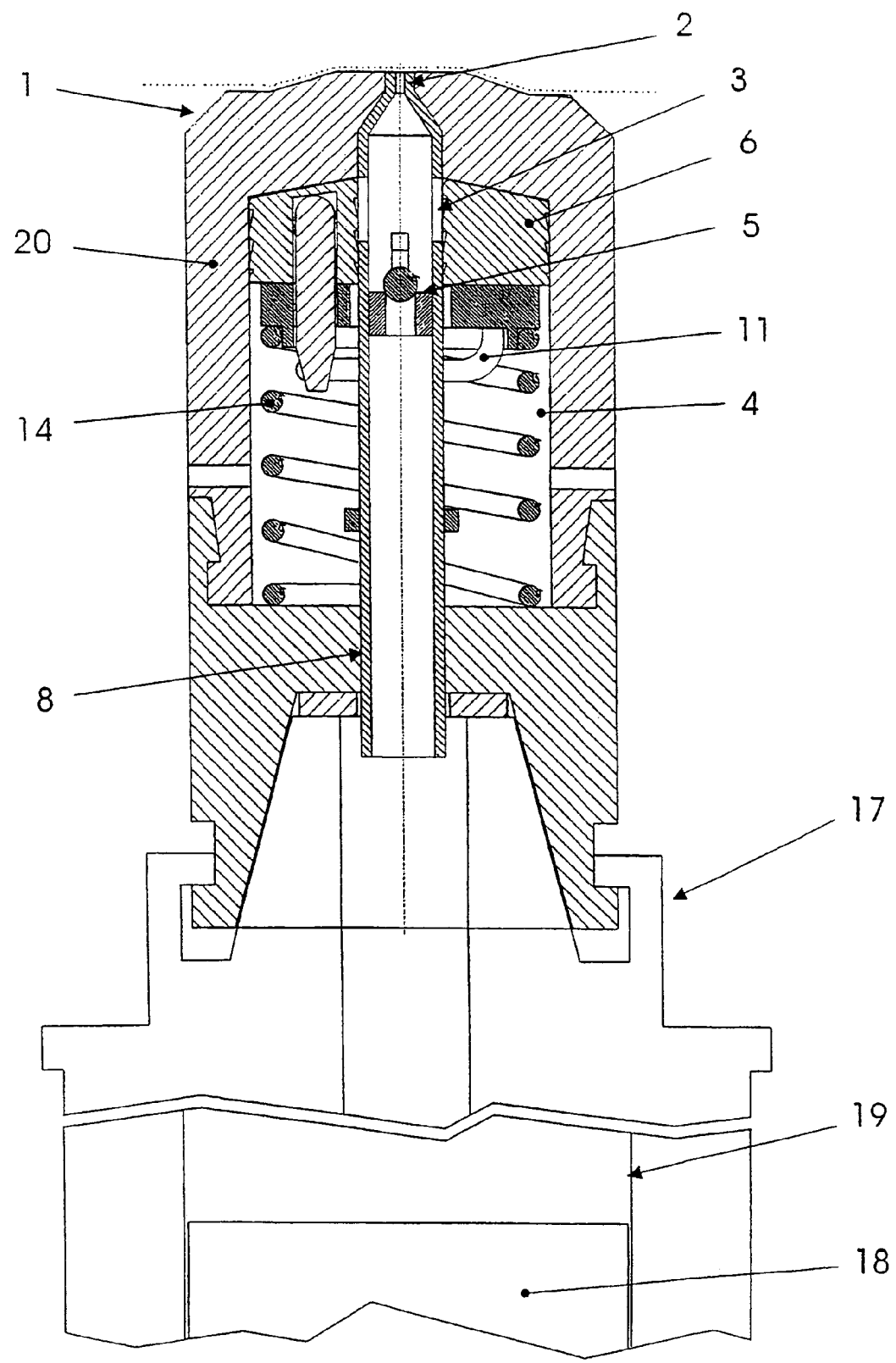
Figure 5:
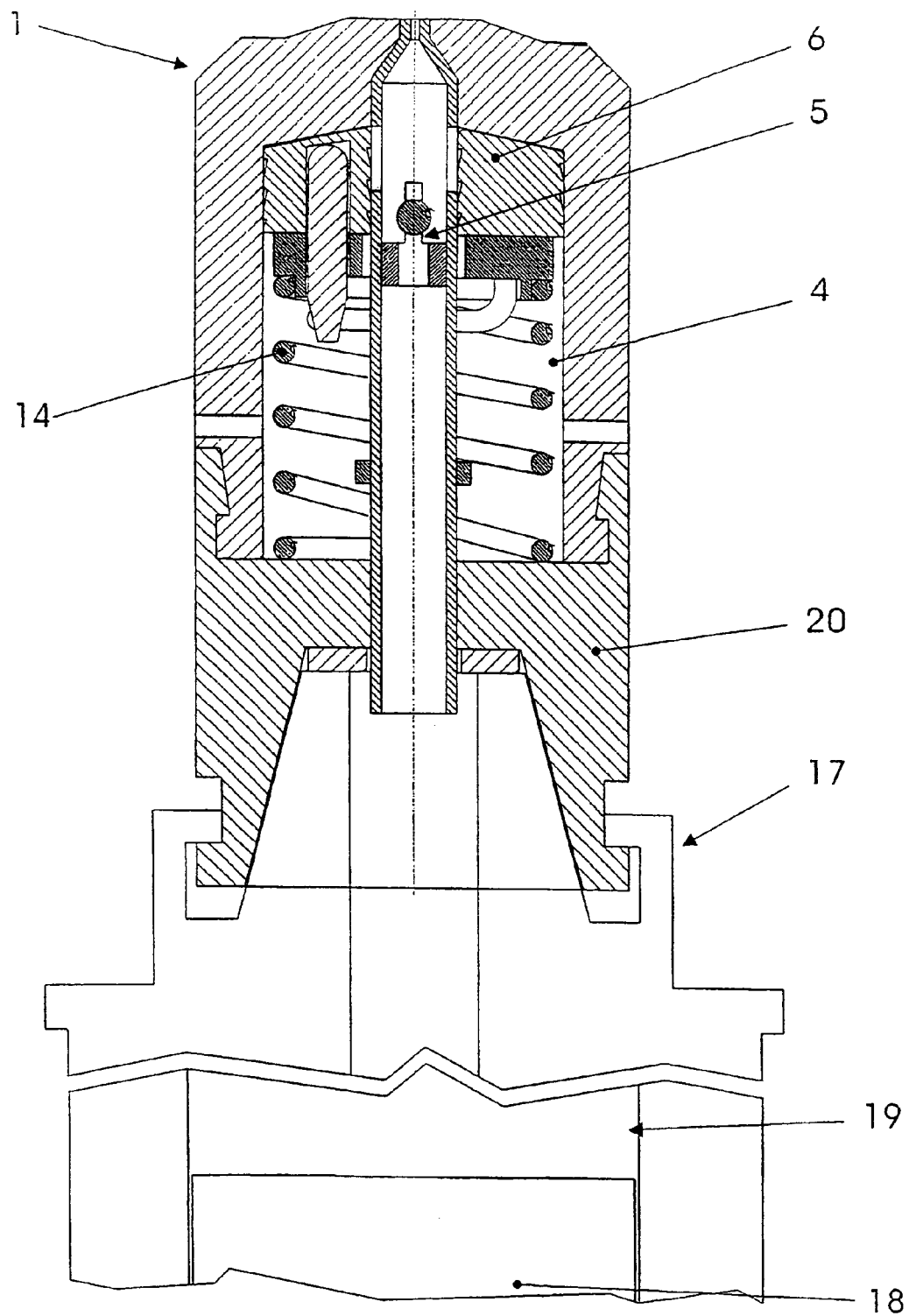
Figure 6:
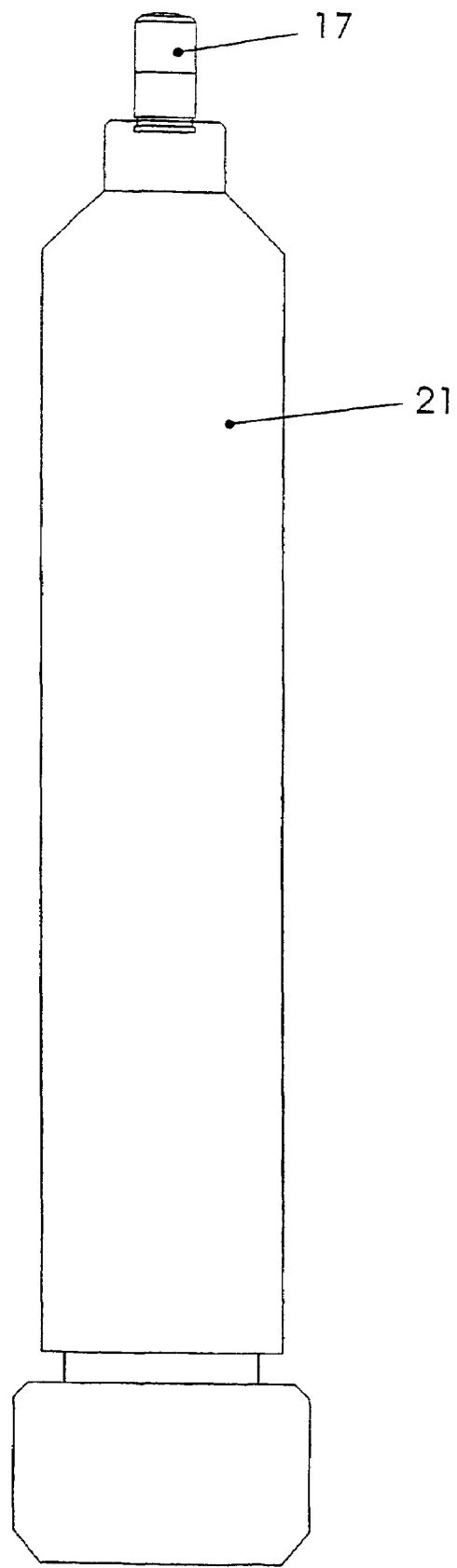
Figure 7:
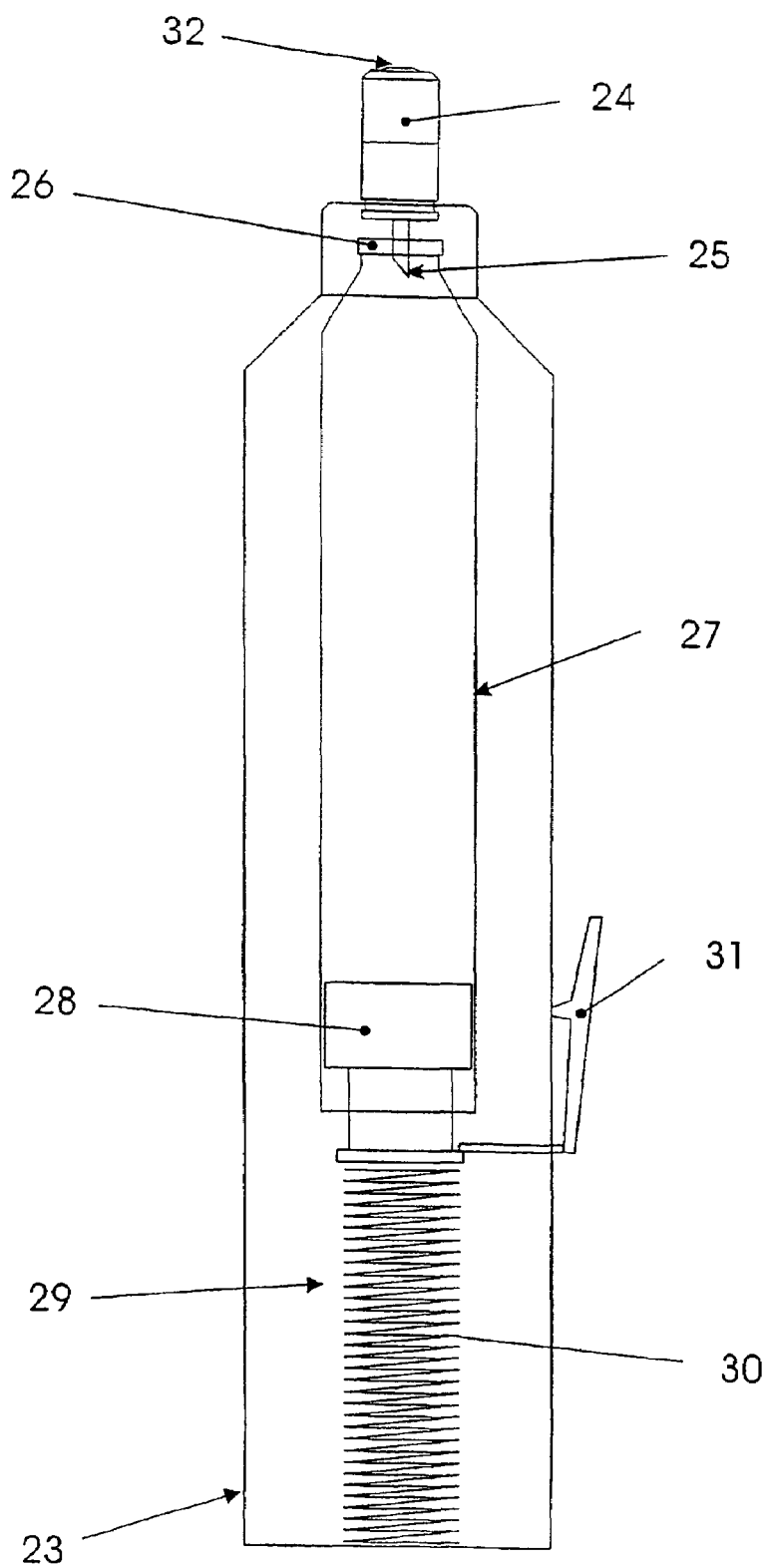
Figure 8:
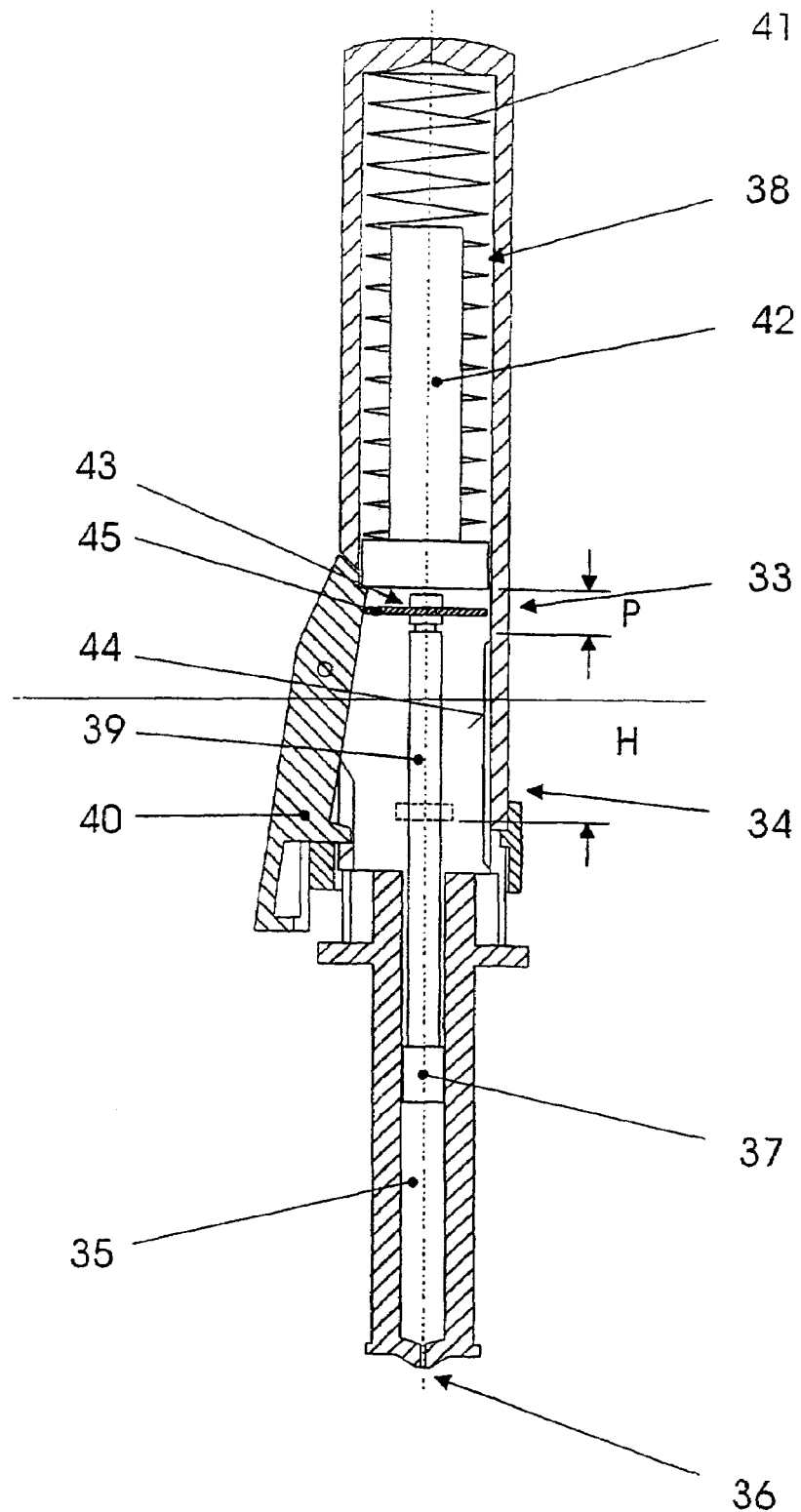
Figure 9:
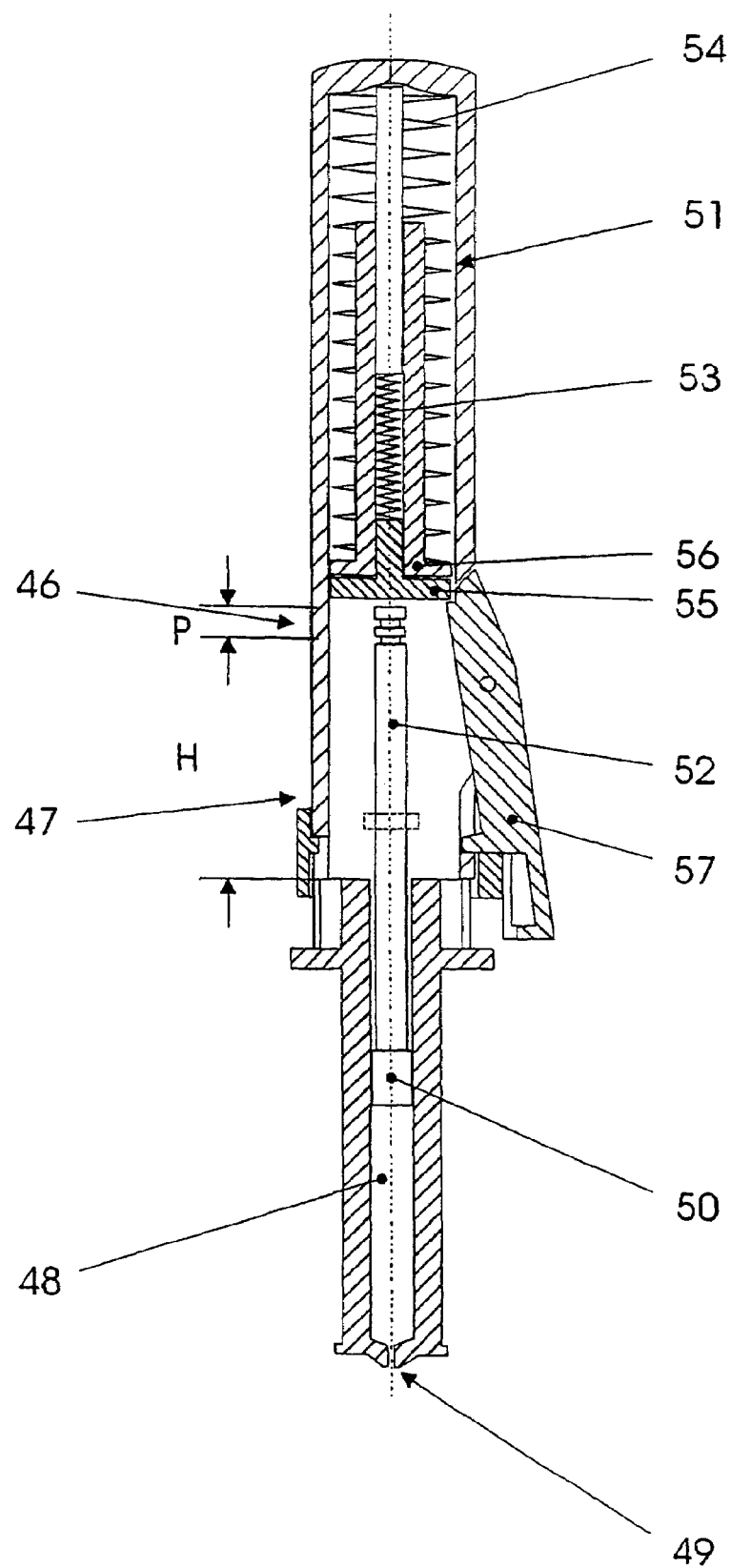

These show:

FIG. 1: a longitudinal cross-section through a pre-injection device of a device according to the invention, FIG. 1a: the cross-sectional view along the line (Ia-Ia) through the pre-injection device from FIG. 1, FIG. 2: a cross-sectional view through the pre-injection device from FIG. 1, with the main injection device attached, in the phase of filling, FIG. 3: a cross-sectional view through the pre-injection device from FIG. 1, in the phase of triggering a pre-injection, FIG. 4: a cross-sectional view through the pre-injection device from FIG. 1, in the phase when the pre-injection is completed, FIG. 5: a cross-sectional view through the pre-injection device from FIG. 1, in the phase after completion of the pre-injection, FIG. 6: another embodiment of a pre-injection device of a device according to the invention, with a PEN system attached, FIG. 7: an embodiment of a pre-injection device of a device according to the invention, with a disposable injection system connected with it, FIG. 8: a longitudinal cross-section through a structural unit of a pre-injection device and a main injection device, FIG. 9: a longitudinal cross-section through another embodiment of a structural unit of a pre-injection device and a main injection device.

FIG. 1 shows a pre-injection device 1, with a main injection device 17 shown with a broken line. The main injection device 17 can be a conventional injection syringe, for example, having a chamber 19 that is delimited by a displaceable piston 18, for accommodating a predetermined amount of a medium to be injected. The main injection device 17 serves to introduce a predetermined amount of the medium to be injected into a tissue of a human or an animal. The pre-injection device 1 produces an injection channel by means of a pre-injection medium. The pre-injection device 1 is mounted on the injection syringe in place of a conventional needle or cannula, in the sense of a needle-free cannula for single use.

The pre-injection device 1 has a base body 20 connected with a channel 8, forming a positive lock, and a chamber 4 for accommodating the pre-injection medium. A channel 8 opens into a nozzle 2. The face of the base body 20 is supposed to serve as a contact surface for the nozzle 2 against the tissue to be injected, during the injection. The starting position of the pre-injection device 1 shown in FIG. 1 starts from an unfilled state of the chamber 4. In this embodiment, initial filling of the chamber 4 is necessary before the injection is performed. In this connection, a partial amount of the medium to be injected, kept supplied in the chamber 19 of the main injection device 17, is used as the pre-injection medium. Alternatively, the chamber 4 of the pre-injection device 1 can already be flooded with a physiologically non-problematic liquid, such as sodium or an anesthetic, in the starting state.

The channel 8 has a connection 3 with the chamber 4, in order to allow filling and emptying of the chamber 4 via the channel 8. Below the connection 3, a kick-back valve 5 is provided in the channel 8, to ensure the freedom from feedback of the pre-injection device 1 relative to the main injection device 17 that is connected via the coupling device 9. In this example, the kick-back valve 5 is configured as a simple ball valve, whereby the control of the kick-back valve 5 takes place automatically during use, by way of the pressure conditions within the pre-injection device 1 and the chamber 19 of the main injection device 17.

The chamber 4 of the pre-injection device 1 must be dimensioned, in terms of its size and its accommodation volume for the pre-injection medium, depending on the planned type of injection (subcutaneous or intramuscular), in such a manner that an injection channel planned in the tissue is produced using a high-pressure jet. For this, a small amount of 0.02 to 0.05 ml, of the pre-injection medium, for example, is already sufficient.

The chamber 4 of the pre-injection device 1 is delimited by a ring-shaped piston 6 that serves for pulse-like ejection of the pre-injection medium as a high-pressure jet. The piston 6 guarantees a seal of the pre-injection medium located in the chamber 4, relative to the surfaces of the channel 8 that border on the chamber 4, and of the base body 20. The piston 6 preferably consists of a duroelastic material having appropriate glide properties, and rests on a pressure plate 7. A pressure-production device 14' having a biased spring 14 is disposed on the side of the pressure plate 7 facing away from the piston 6. Furthermore, a trigger 11, which consists of two stirrup-shaped elements guided in parallel, is anchored in the pressure plate 7. The elements of the trigger 11 are mounted in the pressure plate 7 so as to pivot and under spring force, and are biased against a clamp ring 16 that is rigidly connected with the channel 8, by the spring 14. The elements of the trigger 11 rest against the outside wall of the channel 8 in such a manner that they rest against the clamp ring 16 that is rigidly connected with the channel 8, on the side facing away from the pressure plate 7. In this way, the pressure plate 7, the spring 14, and thereby the piston 6 are held in the biased starting position.

The piston 6 is structured in such a manner that part of its face that borders on the chamber 4 is structured as a membrane 12. The underside of the membrane 12 borders on cavities in the piston 6 and in the pressure plate 7, which are disposed one above the other, with equal coverage. There is a pusher 13 that borders on the underside of the membrane 12 with one end, in these cavities. The second end of the pusher 13 is configured conically and projects between the free ends of the spring elements of the trigger 11.

The membrane 12 is deflected in the direction of the pusher 13 with an increasing pressure in the chamber 4, and displaces the pusher in the direction of the free ends of the spring elements of the trigger 11, until these spring elements are spread apart in such a manner that they can get over the clamp ring 16. With this, the movement of the pressure plate 7 and of the piston 6 is released. The force of the spring 14 is subsequently able to press the pressure plate 7 and the piston 6 into the chamber 4 of the pre-injection device 1. The pusher 13 thereby forms a pressure switch for triggering the pre-injection device 1.

In the case of the pre-injection device 1 shown in FIG. 1, the coupling device 9 for the conical connector to the main injection device 17 configured as an injection syringe is provided. The coupling device 9 can have, for example, a so-called Luer lock standard. For a reliable seal of the coupling of a cone of the injection syringe to the channel 8 of the pre-injection device 1, a seal 10 is provided. The coupling device 9 can assume any desired shape, for connecting other injection systems that can be used once or multiple times, or can also be an integrative part of these systems, as shown in FIG. 6 and FIG. 7, for example.

The action mechanism of the triggering process is illustrated in FIG. 1a, in a cross-sectional view of the pre-injection device from FIG. 1, along the line Ia-Ia. The support effect of the trigger 11 on the clamp ring 16 is cancelled out in that the pusher 13 spreads the two elements of the trigger 11 beyond the region of the clamp ring 16, and the actual triggering process of pre-injection occurs.

The base body 20 is provided with the vent 15, in order to guarantee the function of the pressure-dependent triggering mechanism via the membrane 12 and pusher 13.

FIG. 2 shows the pre-injection device 1 described in FIG. 1 in the phase of filling the chamber 4 with the pre-injection medium. By means of slight manual pressure in the direction of the arrow, as shown, onto the piston 18 of the main injection device 17, the medium to be injected gets into the channel 8, whereby the kick-back valve 5 opens automatically and floods the chamber 4 via the connection 3. In order to assure air-bubble-free filling of the chamber 4 and the channel 8 all the way to the nozzle 2, the filling process is preferably performed in the perpendicular position, until a bubble-free jet exits from the nozzle 2, similar to conventional cannula syringes. Air that is present in the chamber 4 of the pre-injection device 1 escapes via the nozzle 2. The pre-injection device 1 and the main injection device 17, which is connected via the coupling device 9 and configured as an injection syringe are now ready for carrying out the injection into the tissue. In order to initiate the injection, the pre-injection device 1 is pressed onto the tissue to be injected, with its nozzle 2 that opens out of the base body 20, in perpendicular manner.

FIG. 3 shows the status of the pre-injection device 1 at the moment of triggering the pre-injection. By means of manually exerting pressure onto the piston 18 of the main injection device 17 after the nozzle has been set onto the skin of a human or an animal, shown with a dot-dash line, the pressure onto the pre-injection medium in the chamber 4 of the pre-injection device 1 increases. This causes the membrane 12 of the piston 6 to be deflected against the pusher 13, causing it to be moved against the trigger 11. The pusher 13 spreads the two spring elements of the trigger 11 apart with its conically shaped second end, to such an extent that these overcome the edge of the clamp ring 16. The pre-injection is triggered by means of the release of the force of the biased spring 14.

In FIG. 4, the pre-injection device 1 from FIG. 1 is shown after the pre-injection has been completed. In the pre-injection, the piston 6 was moved into the chamber after the movement of the trigger 11, by the force of the spring 14. In this connection, the pre-injection medium was transported through the nozzle 2 in pulse-like manner, out of the chamber 4 through the connection 3 into the channel 8 above the automatically closing kick-back valve 5. In this connection, the pulse-like transport of the pre-injection medium out of the chamber 4 via the nozzle 2 takes place as a high-pressure jet, which produces an injection channel through the skin, shown with a dot-dash line, into the tissue lying underneath.

After the pre-injection is complete, the pre-injection medium has completely escaped from the chamber 4 of the pre-injection device 1. The piston 6 is in the end position and thereby closes the connection 3 to the channel 8 above the kick-back valve 5, and is held in the position shown by the spring 14.

In FIG. 5, the status of the pre-injection device 1 after completion of the pre-injection is shown. In order to obtain the injection channel in the tissue that was produced by the high-pressure jet, the manual pressure on the piston 18 of the main injection device 17 must be maintained further after the pre-injection was performed. By means of the pressure onto the piston 18 of the main injection device 17 in the direction of the arrow, the kick-back valve 5 opens again, and the actual injection via the injection channel that has been produced takes place. In this connection, the piston 6 of the pre-injection device 1 remains in its end position and does not change its position, since the spring 14, which has not been completely relaxed, presses it against the delimitation of the chamber 4.

FIG. 6 shows a variant of the device according to the invention, as a supplement to a so-called PEN system, which is known from the trade and described in the U.S. Pat. No. 5,279,586, for example, a system for simple metering and injection of medications from standard Carpules (e.g. insulin, vaccines). Such systems permit simple pre-adjustment of the desired dose from a Carpule, and an injection by pushing a button, particularly for the use of patients on themselves. In this connection, the PEN system serves as the main injection device 21. This PEN system is preceded by a pre-injection device 22 in place of the needle that is usually used. The pre-injection device 22 is structured as described in FIGS. 1 to 5 and can guarantee needle-free administration, in simple manner, as a supplement to the PEN system known from commerce.

FIG. 7 illustrates a structural unit consisting of a spring-force-driven main injection device 23 and a prior pre-injection device 24 as a disposable injection system for the administration of media administered at higher doses, such as vaccines, etc. In this connection, the pre-injection device 24 can be configured as an integrative or supplemental component of the main injection device 23, and can be structured like the pre-injection device 1 according to FIGS. 1 to 5. As a supplemental component, the pre-injection device 24 preferably has a penetration cannula 25 for penetrating a seal 26, for a connection with a chamber 27 of the main injection device 23 that is configured as a medication reservoir. Such medication reservoirs are frequently referred to as Carpules. The chamber 27 contains the entire dose of the medium to be injected, and possesses a piston 28, which is connected with a pressure-production device 29. In this example, the biased spring 30 is used to produce the injection pressure. In the case of activation of a trigger 31, the force of the spring 30 of the pressure-production device 29 is released to the piston 28 and results in the exertion of pressure on the medium that is located in the chamber 27. With this device, the manual exertion of pressure onto the piston, as in the case of a conventional injection syringe, is simulated in appropriate manner. The pressure increase in the chamber 27 has the result, as described with regard to FIGS. 1 to 5, of triggering the pre-injection in the pre-injection device 24, through a nozzle 32. As a result of the injection channel thereby produced in the skin, the entire amount of medication is introduced into the tissue, up to the end position of the drive piston 28, in other words with emptying of the chamber 27.

FIG. 8 shows a longitudinal cross-section through a device for needle-free injection of a medium into a tissue, having a unit of a pre-injection device 33 and a main injection device 34, in which a single chamber 35 for accommodating a medium to be injected has a nozzle 36 intended to be set onto the skin, and delimited by a piston 37. The piston 37 is connected with a piston rod 39 that is guided to a pressure-production device 38. A trigger 40 that can be manually activated holds a pressure piece 42, biased by a spring 41, in the position shown. When the trigger 40 is activated, the movement of the pressure piece 42 is released, and the pressure piece 42 is pressed against the piston rod 39 by the spring 41. In this connection, the piston 37 is pushed into the chamber 35 and the medium to be injected, which is located in the chamber 35, is ejected from the nozzle 36. The movement of the piston 37 is controlled by damping means 43, in such a manner that at first, in a first step, it is moved a short distance at a high pressure, and in a second step, it is moved at a low pressure, by a great distance, into the chamber 35. The first step serves as the pre-injection and is indicated with P in the drawing, while the second step, as the main injection, is indicated with H. With this, as in the preceding embodiments, an injection channel is first produced in a pre-injection, and then, a planned amount of the medium to be injected is introduced into the tissue with a main injection. In the case of the pre-injection, a volume of 0.02 to 0.05 ml, for example, can be ejected, while in the case of the main injection, up to several ml can be injected into the tissue. The chamber 35 can therefore have a volume of several ml. As damping means 43, the piston rod 39 has a damping disk 45 that stands opposite a fixed damping track 44, as an example. For the remainder, the device is configured for one-time injection and structured as described in WO 01/36028, so that explicit reference is made to this document for the further disclosure.

FIG. 9 shows another embodiment of a device for injecting a medium into the tissue of a human or an animal, having a unit of a pre-injection device 46 and a main injection device 47, in which a single chamber 48 is provided with a nozzle 49 and delimited by a piston 50. The piston 50 has a piston rod 52 that is guided up to a pressure-production device 51. The pressure-production device 51 has two pressure pieces 55, 56, each biased by a spring 53, 54, respectively. The pressure pieces 55, 56 are held by a trigger 57 that can be manually activated. The first spring 53 has a short spring path and a high spring stiffness, while the second spring 54 has a long spring path and a low spring stiffness. When the trigger 57 is activated, the first spring 53 moves the piston rod 52 and thereby the piston 50 by the distance P, at a great force, because of the greater spring force. In this connection, if the nozzle 49 is set onto the skin, an injection channel is produced in the tissue by means of a pre-injection. In a second step, the second spring presses the piston rod 52 by the distance H, in the direction of the chamber 48. In this connection, the entire amount of the medium to be injected that is located in the chamber 48 is pressed out of the nozzle 49 at a low pressure. This characterizes the main injection, during which several ml of the medium to be injected can be introduced into the tissue, through the injection channel that was produced during the pre-injection. Therefore, in the case of this device, as well, the chamber 48 can have a volume of several ml. For the remainder, the device is configured for one-time injection and struc-

The invention claimed is:

1. A device for needle-free injection of a medium into the tissue of a human or an animal, comprising a needle-free injection device comprising a first chamber accommodating a pre-injection medium for production of a high-pressure jet of the pre-injection medium for producing an injection channel by means of a high pressure and a small volume, and a main injection device comprsing a second chamber accommodating a medium to be injected, the second chamber medium being injected with a great volume and a low pressure in comparison with the volume and pressure of the pre-injection device; wherein a nozzle intended to be set onto the skin is connected with the chamber of the pre-injection device and with the outlet of the main injection device by way of a kick-back valve, and wherein a pressure-production device that is connected with the chamber of the pre-injection device is configured to produce a high-pressure jet from the nozzle that penetrates the tissue, whereby the chamber of the pre-injection device has a volume sized exclusively for producing an injection channel in the tissue, and the chamber of the main injection device ha a volume intended for the medium to be injected; wherein the pre-injection device further comprises a piston; and whrein a membrane is part of the piston, with which the chamber of the injection medium is connected, wherein a pusher is located inside the piston, and wherein when the pressure in the chamber increases, said membrane is deflected in the direction of the pusher to activate the trigger by the way of the pusher.

2. The device as recited in claim 1, wherein the chamber of the main injection device accommodating a predetermined amount of the medium to be injected has a piston that can be moved by hand.

3. The device as recited in claim 1, wherein the pressure-producing device of the pre-injection device has a movable pressure plate biased by a spring force, or a biased pressure piece, wherein the movable pressure plate is pressed into a pre-injection device.

4. The device as recited in claim 1, wherein the pre-injection device has a channel connected with the nozzle at one end and the chamber of the main injection device containing the injectable medium at the other end.

5. The device as recited in claim 1, wherein a kick-back valve is disposed within the channel below the connection to the chamber of the pre-injection device.

6. The device as recited in claim 1, wherein the trigger of the pre-injection device holds a moveable pressure plate biased by a spring or a pressure piece in its base position.

7. The device as recited in claim 1, wherein the trigger is connected with the chamber of the pre-injection device and is configured to release the movable pressure plate above the planned pressure.

8. The device as recited in claim 1, wherein the channel has a connection with the chamber of the pre-injection medium, and wherein the kick-back valve is disposed between the connection and the coupling device.

9. The device as recited in claim 1, wherein the chamber has a piston that resets against the movable pressure plate and can be displaced in length, and wherein the channel is guided through the piston and the movable pressure plate.

10. The device as recited in claim 1, wherein the main injection device and the pre-injection device have a common nozzle.

11. The device as recited in claim 1, wherein the trigger of the pre-injection device can be indirectly activated by the pressure produced by the main injection device deflecting the membrane of the pusher.

12. The device as recited in claim 1, wherein the pre-injection device and the main injection device have a common chamber for accommodating the medium to be injected, and a common pressure-production device, wherein the pressure-production device has means for reducing the size of a first, slight part of the chamber in a first step, by a small volume, at a great pressure, and, in a second step, by a great volume, at a low pressure, and wherein the common pressure-production device has a single spring and damping means for damping the movement of a piston that delimits the common chamber, said damping means comprising a piston rod having a damping disk that stands opposite a fixed damping track.

13. The device as recited in claim 1, wherein the common pressure-production device has two springs having different spring stiffness values and spring paths, whereby a first spring element for moving the piston in the first step has a high spring stiffness and a short spring path, while a second spring for moving the piston has a low spring stiffness and a long spring path.

14. The device as recited in claim 1, wherein the pre-injection medium is a physiologically non-problematic liquid.

15. The device as recited in claim 1, wherein the pre-injection medium is the medium to be injected or an anesthetic.

16. A device for needle-free production of an injection channel in the tissue of a human or an animal, for introduction of a medium to be injected into the tissue, comprising a pre-injection device; and a main injection device that contains the medium to be injected, wherein the pre-injection device comprises a chamber for accommodation of a pre-injection medium and has a nozzle intended to be set onto the skin, and the pre-injection device further comprises a pressure-production device for producing a high-pressure jet of the pre-injection medium that exits from the nozzle, and a piston wherein the chamber has a volume sized exclusively for producing the injection channel, and wherein the piston further comprises a membrane, with which the chamber of the injection medium is connected, wherein a pusher is located inside the piston, wherein when the nozzle is inserted onto the skin of a patient the pressure in the chamber increases, causing said membrane to be deflected against the pusher, causing the pusher to be moved against a trigger to activate the trigger.

17. The device as recited in claim 16, wherein the pre-injection device has a coupling device for a connection with the main injection device that contains the medium to be injected.

18. A method for needle-free injection of a medium into human or animal tissue comprising the steps of:
(a) providing a device comprising a needle-free pre-injection device comprising: a piston; a first chamber accommodating a pre-injection medium for production of a high-pressure jet of the pre-injection medium for producing an injection channel with a high pressure and a small volume and a main injection device comprising a second chamber accommodating a medium to be injected, the medium being injected with a great volume and a low pressure in comparison with the volume and pressure of the pre-injection device;
(b) first producing the high-pressure ject of the pre-injection medium via the needle-free pre-injection device;
(c) producing the injection channel with the high-pressure jet; and (d) subsequently introducing the medium to be injected into the tissue through the injection channel; wherein a nozzle intended to be set onto the skin is connected with the chamber of the pre-injection device and with the outlet of the main injection device by way of a kick-back valve, and wherein a pressure-production device that is connected with the chamber of the pre-injection device is configured to produce a high-pressure jet from the nozzle that penetrates the tissue, whereby the chamber of the pre-injection device has a vlume sized exclusively for producing an injection channel in the tissue, and the chamber of the main injection device has a volume intended for the medium to be injected; wherein a membrane is part of the piston, with which the chanber of the injection medium is connected, wherein a pusher is located inside the piston, and when the pressure in the chamber increases causing said membrane to be deflected in the direction of the pusher to activate the trigger by way of the pusher.

19. The method as recited in claim 18, wherein the introduction of the medium to be injected directly follows the production of the injection channel, and wherein a minimum pressure is applied during the introduction of the medium to be injected, to maintain the injection channel.

20. The method as recited in claim 18, wherein the production of the injection channel takes place at a high pressure and a low volume, and wherein the introduction of the medium to be injected takes place at a high volume and low pressure.

21. The method as recited in claim 18, wherein the pressure for producing the injection channel is applied by means or spring force, and wherein the pressure for injection of the medium to be injected is applied manually.

* * * * *